United States Patent [19]
Eek et al.

[11] Patent Number: 5,961,305
[45] Date of Patent: Oct. 5, 1999

[54] PUMP CHAMBER AND VALVE FOR A PUMP CHAMBER

[75] Inventors: Arne Eek, Trosa; Billy Nilson, Mjölby, both of Sweden

[73] Assignee: Astra AB, Sweden

[21] Appl. No.: 08/649,624

[22] PCT Filed: Feb. 12, 1996

[86] PCT No.: PCT/SE96/00173

§ 371 Date: May 23, 1996

§ 102(e) Date: May 23, 1996

[87] PCT Pub. No.: WO96/25189

PCT Pub. Date: Aug. 22, 1996

[30] Foreign Application Priority Data

Feb. 15, 1995 [SE] Sweden ................................. 9500557

[51] Int. Cl.⁶ ................................................. F04B 39/10
[52] U.S. Cl. ........................... 417/566; 417/569; 137/517
[58] Field of Search ................................ 417/274, 413.1, 417/569, 566; 92/129, 99, 100, 101; 137/517

[56] References Cited

U.S. PATENT DOCUMENTS

| | | | |
|---|---|---|---|
| 4,507,062 | 3/1985 | Wally | 417/413 |
| 5,388,615 | 2/1995 | Edlund et al. | 137/859 |
| 5,437,218 | 8/1995 | Papin | 92/13.2 |

FOREIGN PATENT DOCUMENTS 398583  11/1990  European Pat. Off. ....... A61M 5/142

OTHER PUBLICATIONS

Dialog Abstract of EP patent document 601,491 (listed above as document AM1), Derwent World Patents Index accession number 94–184921/199423.

*Primary Examiner*—Charles G. Freay
*Attorney, Agent, or Firm*—Vinson & Elkins L.L.P.

[57] ABSTRACT

The present invention relates to a pump chamber (1) for a pump intended primarily for infusion systems for medical use, said pump chamber comprising walls (21, 28) delimiting said chamber and an inlet (22) and an outlet (23), a part of said walls of said pump chamber being formed by a flexible membrane (40, 90), said membrane being actuatable by a reciprocally movable actuating means (80), thus varying the volume of the pump chamber in accordance with the movements of said actuating means. The membrane (40, 90) has a convex domed shape projecting outwardly from said pump chamber (1) and is made of a resiliently flexible material, the apex of the domed membrane being acted upon by said actuating means, said actuating means having a stroke which may be adjusted to the amount of the dose to be administered. The invention also relates to a valve for a pump chamber.

12 Claims, 11 Drawing Sheets

PUMP CHAMBER AND VALVE FOR A PUMP CHAMBER

TECHNICAL FIELD OF THE INVENTION

The present invention relates to a pump chamber for a pump intended primarily for infusion systems for medical use, said pump chamber comprising walls delimiting said chamber and an inlet and an outlet, a part of said walls of said pump chamber being formed by a flexible membrane, said membrane being actuatable by a reciprocally movable actuating means, thus varying the volume of the pump chamber in accordance with the movements of said actuating means.

BACKGROUND TO THE INVENTION

Compositions comprising pharmaceutically-active compounds in a liquid or dissolved state are often administered by means of infusion systems, the most simple being an infusion bag with a flexible tube which is connected to an injection needle to be inserted into a vein or similar. The driving force in such a system is gravity. A simple gravity-actuated system is relatively inexact and hence may not be sufficient for the purposes of administering certain active compositions having high requirements regarding exact dosage, both momentarily and during a length of time. The dosage may be very small and the dosing thereof may be extended over a long period of time, which sets a high standard regarding the precision of the delivery system.

There is also a demand for delivery systems, in which the patient can influence or control the dosage of the drug (PCA, Patient Controlled Analgesia), for instance in systems for delivering an anaesthetic or analgesic compositions.

Relatively sophisticated pumps have been developed to meet these standards. However, such pumps, which operate by depressing the infusion tubing, are expensive and complicated to manufacture and to use. Some pumps of this kind are for instance described in U.S. Pat. No. 3,985,133 and U.S. Pat No. 4,396,385.

A pump apparatus comprising a separate pump chamber operable by means of a piezoelectric actuating means and magnetically biassed valve means is known from EP-A-0 398 587. Again, this kind of pump is relatively complicated to manufacture and to use.

For the sake of sterility it also is highly desirable to have a pump which may be designed to be disposable, at least as far as the parts being directly in contact with the active composition are concerned. Pumps utilizing separate, disposable pump parts are for instance disclosed in U.S. Pat. No. 4,140,118, U.S. Pat. No. 4,273,121 and U.S. Pat. No. 4,474,309.

However, in order to be economically viable, the disposable parts have to be inexpensive to manufacture whilst retaining the properties regarding the dosage precision, both momentarily and continuously.

Consequently, one problem to be solved by the invention is to provide a device which whilst being simple to use, is able to dose the active composition in question with extreme exactness, may be manufactured inexpensively as a disposable part and is suitable for use in a PCA-system.

Another problem to be solved by the present invention is also related to the desire for simplicity of use and design of the device, namely the facilitation of the removal of the air initially present in the infusion tubing and in the pump chamber when the pump chamber is being connected into the infusion system. Standard infusion pumps typically require sophisticated detection mechanisms which warn against the presence of air in the infusion tubing. A device, in which it is physically impossible to infuse air into a patient during normal operation, thus eliminating the need for such a detection mechanism, is therefore highly desirable.

Portable infusion pumps normally utilize special cassettes which mostly have to be filled with active compositions(s) at a pharmacy under sterile conditions, which may be costly and inconvenient for the patient. Consequently, there is also a need for portable infusion pumps which may be used with standard prefilled infusion bags which are relatively inexpensive, readily available and which may be delivered in sterile packs.

SHORT DESCRIPTION OF THE INVENTIVE CONCEPT

According to the invention there is provided a pump chamber for a pump for the administration of active compositions, said pump chamber comprising walls delimiting said chamber and an inlet and an outlet, a part of said walls of said pump chamber being formed by a flexible membrane, said membrane being actuatable by a reciprocally movable actuating means, thus varying the volume of the pump chamber in accordance with the movements of said actuating means, characterized in that said membrane has a convex domed shape projecting outwardly from said pump chamber and is made of a resiliently flexible material, the apex of the domed membrane being acted upon by said actuating means, said actuating means having a stroke which may be adjusted to the amount of the dose to be administered.

In particular, we have found that the device according to the invention may deliver doses of active compositions with a degree of exactness which far exceeds conventional, gravity actuated systems, such as those described hereinbefore.

We prefer that the apex of the domed membrane is provided with a part which is to be acted upon by the actuating means. The part, which may comprise a stiff plate, may be in the shape of a secondary, smaller dome projecting outwardly from the membrane. Such a part may easily be adapted to the volume of the dose of composition. We have found that a domed membrane comprising such a part may facilitate dosing of active compositions with extreme accuracy and reproducibility.

The aforementioned domed membrane may be actuated manually or mechanically. We prefer the actuating means to comprise a reciprocally and longditudinally moveable piston.

The piston may be reciprocally and londitudinally moved by means of a rotatable shaft and cam mechanism, which cam mechanism converts the rotary motion of the shaft to a reciprocating motion of the piston.

For example, the actuating means may comprise a rotatable shaft having one end in contact with one end of the aforementioned piston which may be located along the axis of rotation of the shaft. The piston may be free to move translationally along, though not to rotate about, the axis of rotation of the shaft. The resilience of the domed membrane may be provide sufficient bias to maintain contact between the shaft and the piston. The mutually contacting ends of the piston and the shaft may be equipped with cam surfaces such that rotation of the shaft, coupled with the bias provided by the domed membrane, enables the piston to move reciprocally.

The inlet outlet of the pump chamber may be positioned in parallel at opposite ends of the chamber such that the direction of flow of liquid into and out of the chamber is the same. However, from the point of view of compactness, we prefer the inlet and outlet to be positioned such the direction of flow of liquid out of the chamber is orthogonal to that of the flow into the chamber.

According to the invention, the above problems may be further solved by providing a valve for a pump chamber which allows air, but not liquid, to flow from the pump chamber.

Preferred embodiments of the above aspects of the invention are set forth hereinafter.

SHORT DESCRIPTION OF THE APPENDED DRAWINGS

DETAILED DESCRIPTION OF PREFERRED EMBODIMENTS OF THE INVENTION

Figure 1:
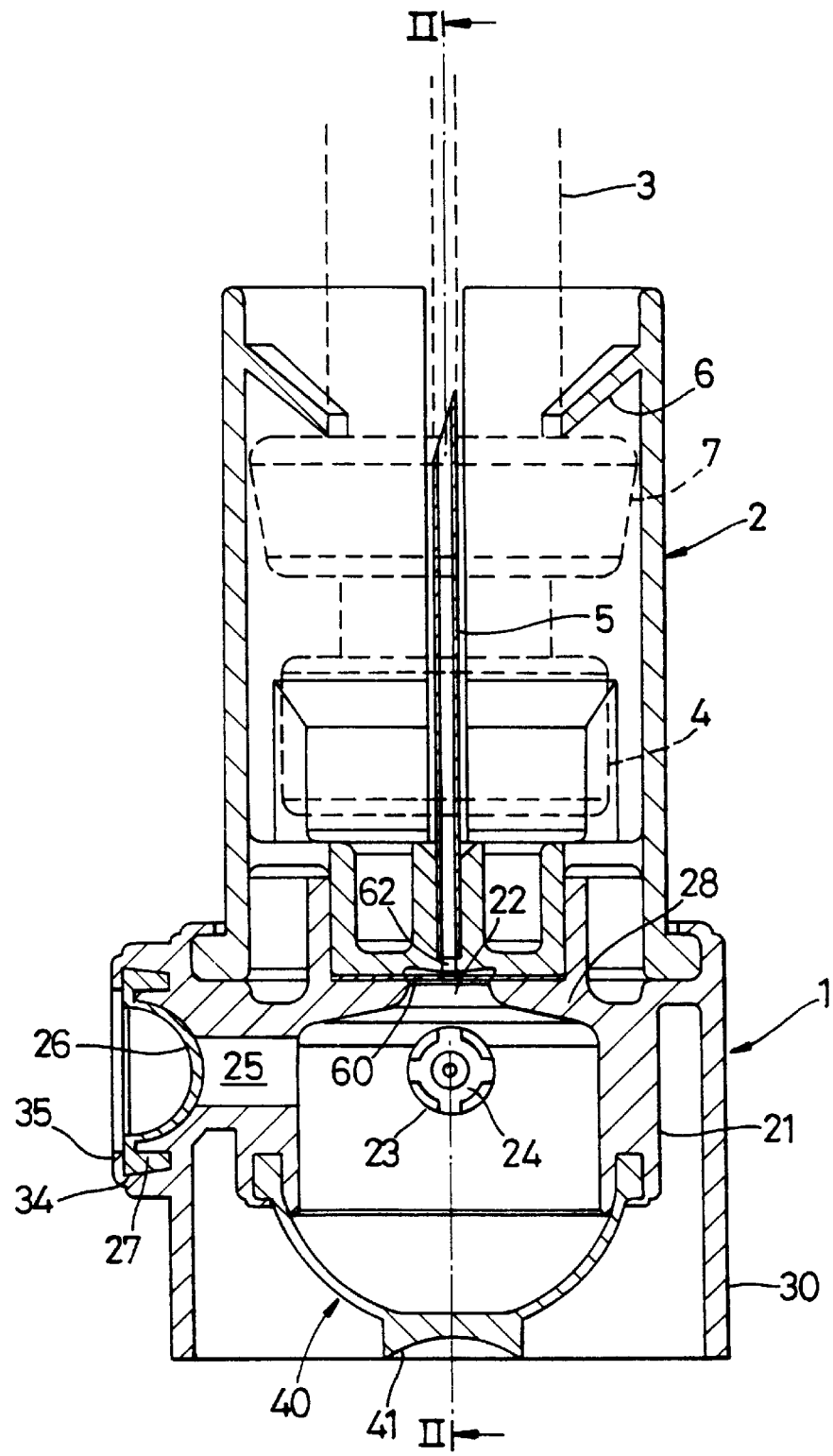
FIG. 1 shows a section of a pump chamber according to the invention.
Figure 2:
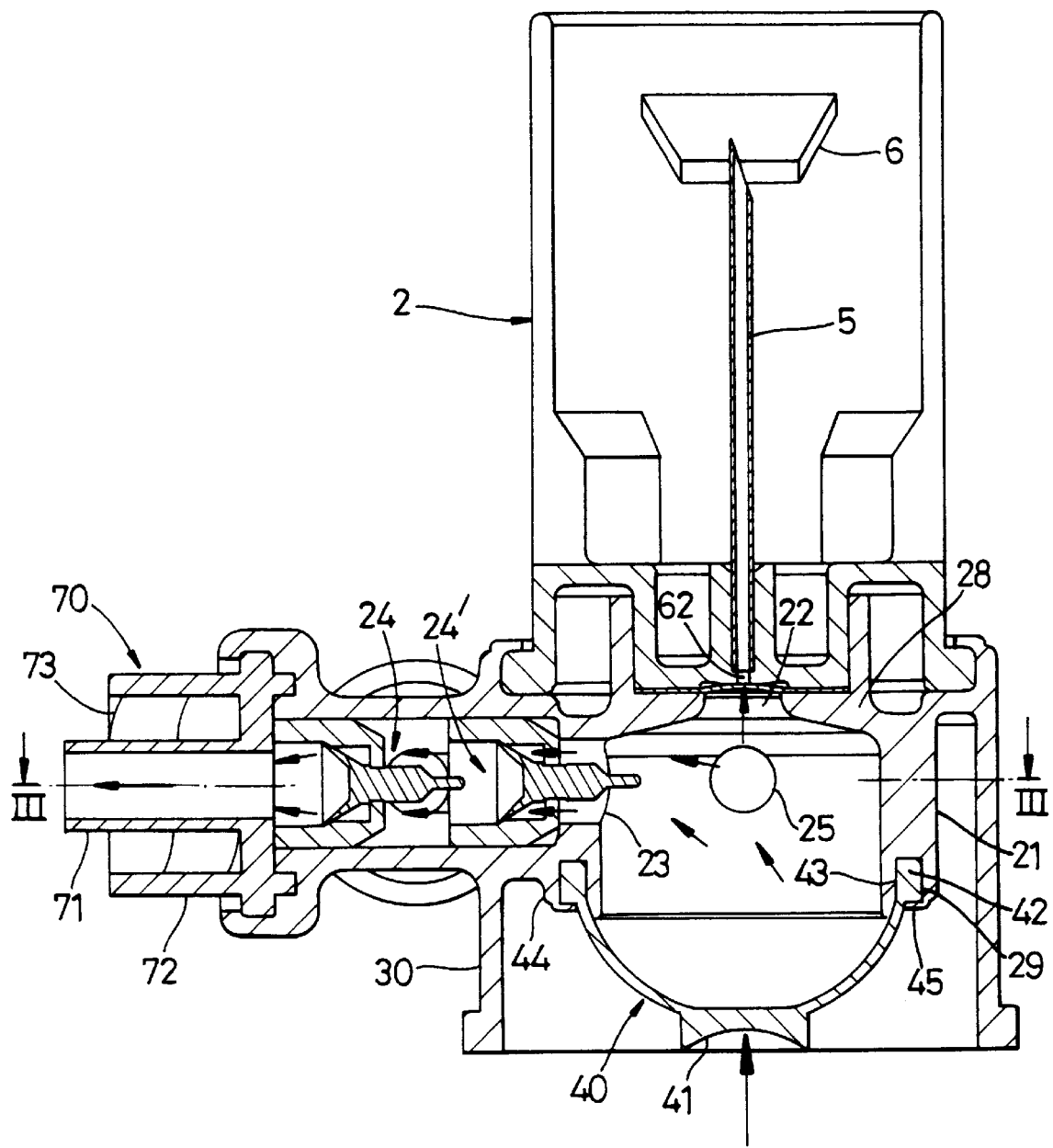
FIG. 2 is a section of the pump chamber in FIG. 1 taken along the line II—II in FIG. 1.
Figure 3:
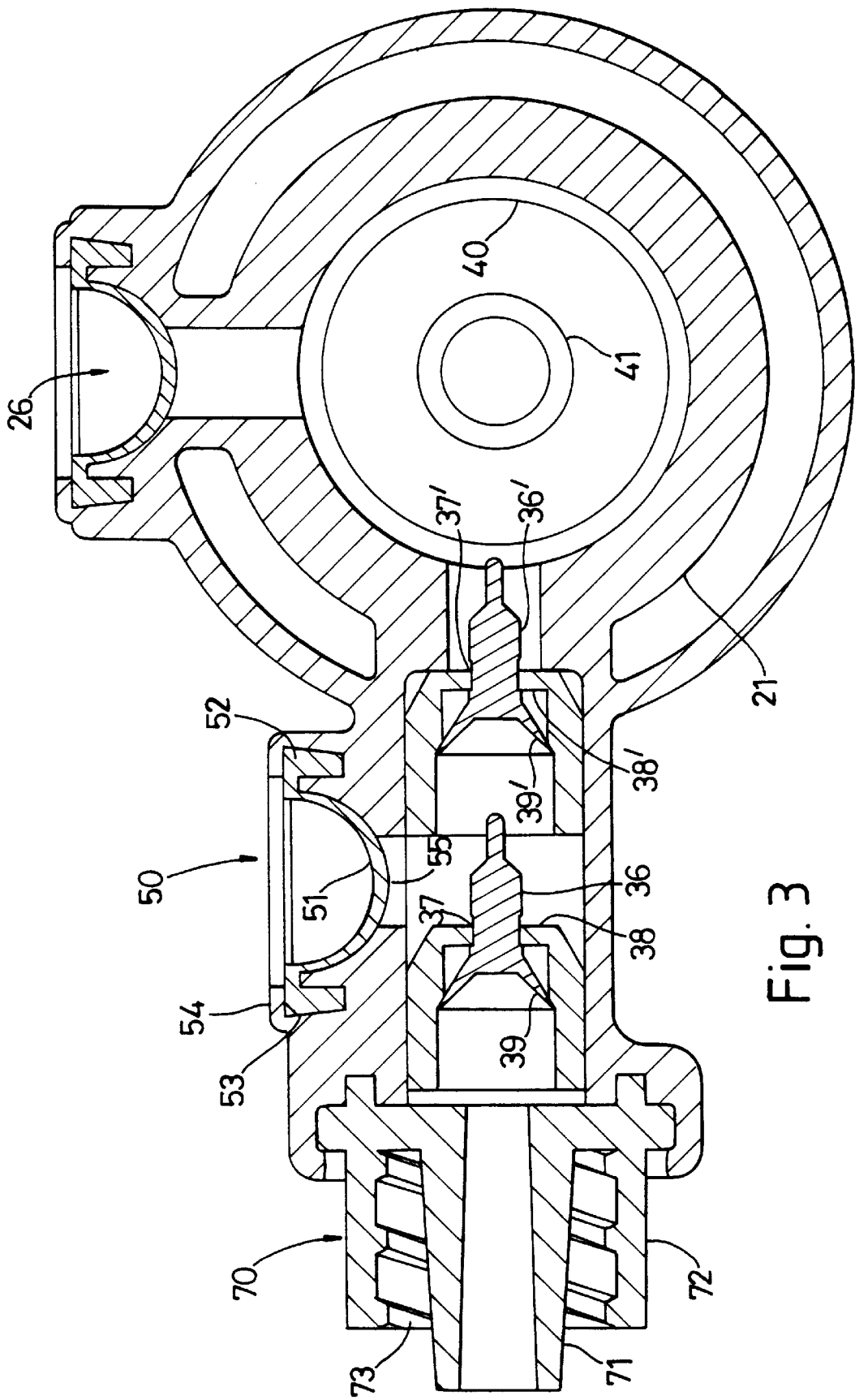
FIG. 3 is a section along the line III—III in FIG. 2.

As illustrated in FIGS. 1–3, the preferred embodiment of the pump chamber comprises a housing 1 provided with a tubular connecting part 2 for connection to a standard infusion bag 3 (the connective parts of the bag being indicated with a dashed line). In use, the infusion bag is located above the pump chamber. The infusion bag may be provided with a standard rubber or plastic seal 4 to be penetrated by a hollow, standard type needle 5 (or by hollow, standard type conical piercing means) in contact with an inlet conduit 62 and located within the connecting part 2, as is quite conventional in the art of infusion systems. The connecting part 2 also includes retaining means 6 engaging a flange portion 7 on the infusion bag, the retaining means 6 preventing the re-use of the disposable pump chamber by locking the bag in the connecting part 2 or by causing the connecting part 2 to be damaged upon forcible removal of the bag. The retaining means 6 slope obliquely downwards and additionally serve to guide and center the connective parts of the infusion bag down onto the needle 5.

The housing 1 is also provided with connecting means 70 with an outlet 23 for connection to an infusion tubing including an injection needle or other means for connection to the patient, see for instance FIG. 2. In this particular embodiment the connecting means comprises a standard "luer" cone 71 with locking means 72 in the form of a cylindrical part tapering internally and with interior threads 73 (a so-called "luer lock").

The pump chamber comprises a cylindrical wall 21 and a circular end wall 28. An inlet 22 in fluid connection with the hollow needle 5 is disposed centrally in the end wall 28. In the normal working position of the pump chamber, the inlet 22 may be oriented upwards, towards the infusion bag.

A domed, resilient membrane 40 forms one wall part of the pump chamber. The membrane is convex as seen from the outside of the pump chamber, i. e. the membrane extends outwardly from the pump chamber. In the preferred embodiment the membrane generally has the shape of a spherical segment. The edge of the membrane is provided with a bead 42 fitting into a circumferential groove 29 in the end surface of the cylindrical wall. The depth of the groove is larger than the height of the bead, which means that the upper part 45 of the outer wall 44 of the groove can be crimped over the bead. The inner wall 43 of the groove is shaped to conform with the inside shape of the (spherical) membrane. The membrane is surrounded by a rigid, cylindrical protective wall 30.

When the pump is to be used, the domed membrane 40 is deformed from the outside, either manually or mechanically by a reciprocally movable actuating means. The apex of the membrane is provided with a part designed to be acted upon by said actuating means and is in this particular embodiment designed as a relatively stiff plate 41, preferably formed integrally with said membrane, and which is located on the outside of said domed membrane 40. The plate is symmetrical relative to the apex of said domed membrane and is provided with an outwardly facing concave shape corresponding to a convex shape on the actuating means.

The actuating means preferably is in the form of a reciprocally and longitudinally movable piston 80, see FIGS. 5B–5E, but may be any means giving the plate a distinct and exact translatory movement, and may for instance be a rocker arm with a spherical part rotating in the concave shape of the plate.

Figure 9A:
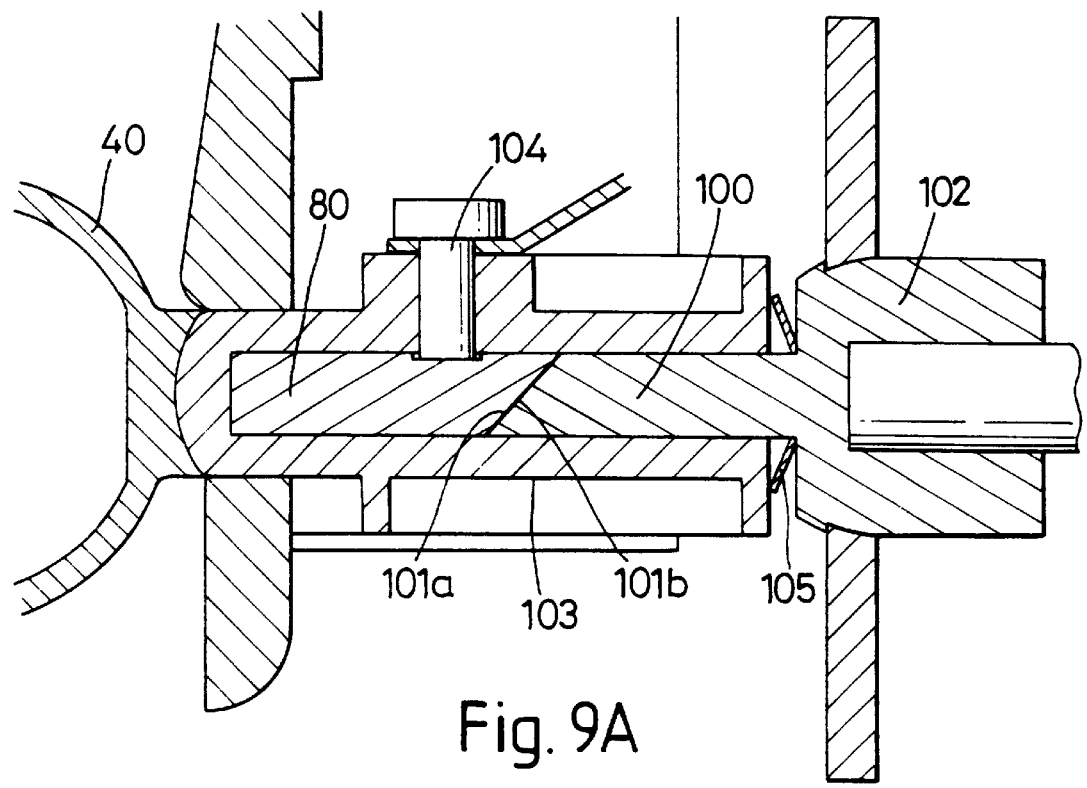
FIGS. 9A and 9B illustrate a preferred embodiment of an actuating means in section
Figure 9B:
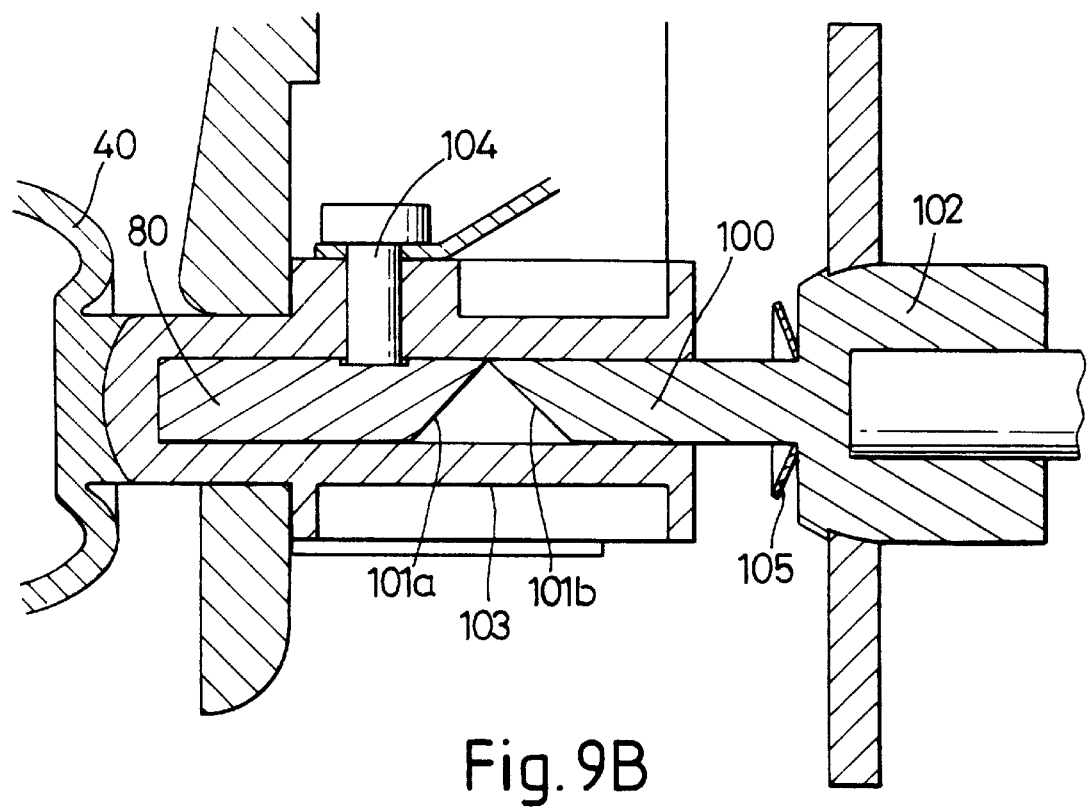

Alternatively, and as illustrated in FIGS. 9A and 9B, the actuating means may be in the form of rotatable shaft 100 having one end in contact with the piston 80, located along the axis of rotation of the shaft, wherein the mutually contacting ends of the piston and the shaft are equipped with cam surfaces.

In the embodiment shown in FIGS. 9A and 9B, the cam surfaces 101a and 101b of of the rotatable shaft 100 and the piston 80 respectively comprise ends cut to a predetermined angle both of which are less than 90°.

The shaft 100 further comprises a connecting ring 102 which is connected to a motor (not shown). The piston 80 is prevented from rotating by a sheath 103 held in position by a pin 104. The resilient nature of the dome 40 provides a biassing means against forward motion of the piston 80, thus maintaining contact between the piston and the shaft 100.

In FIG. 9A the actuating means is at a first position in which the ends of the shaft 100 and the piston 80 are in complete contact with each other. Rotation of the shaft 100 by 180°, as shown in FIG. 9B, forces the piston 80 forward as far as it will go (ie to a second position) by virtue of the cam surfaces 101a and 101b, This translational movement results in depression of the dome 40 of the pump chamber.

Continued rotation of the shaft 100 by a further 180° coupled with the bias of the dome 40 causes the piston 80 to revert back to the first position.

A spring 105 located at the front of the connecting ring 102 prevents the sheath 103 from impacting the connecting ring 102.

The inlet 22 of the pump chamber is provided with a check valve 60 permitting liquid to pass from the needle 5 into the pump chamber, but allowing air to pass both in and out from the chamber.

Figure 4:
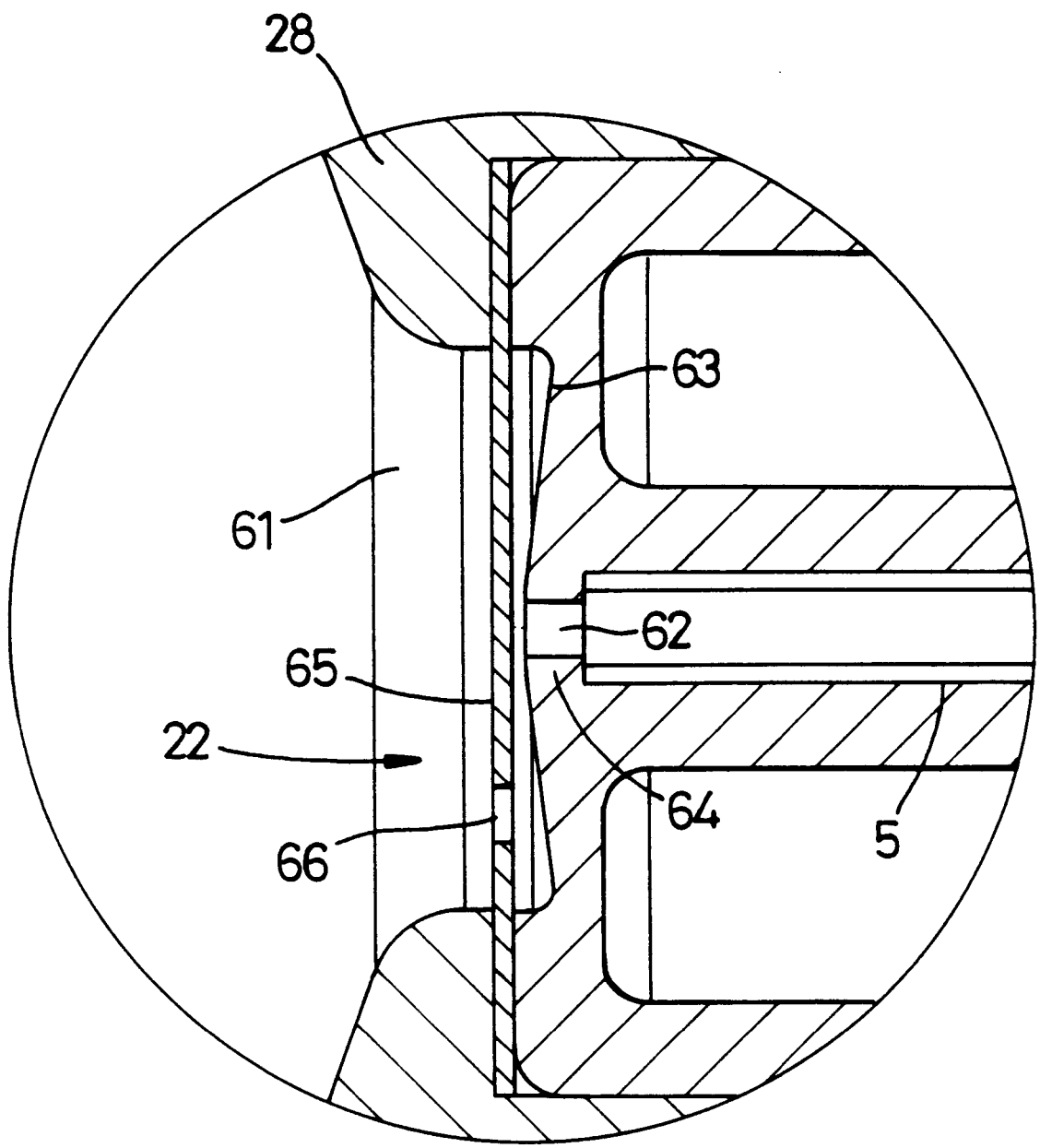
FIG. 4 illustrates a check valve in the inlet to the pump chamber.

The details of the check valve 60 are more clearly shown in FIG. 4. The inlet 22 is designed with a wide recess 61 formed in the inside of the end wall 28 around the inlet 22 and surrounding the inlet conduit 62. The peripheral parts 63 of the recess are deeper than the central part 64. The inlet conduit 62 is located in the central part 64. In this particular embodiment, the central part 64 has a conical shape and the inlet conduit 62 is located in the tip of the central part 64. A resilient, tensioned membrane 65 is mounted over the opening of the recess 61. The membrane 65 is provided with an opening 66 which is located within the area of the recess 61, but offset in relation to the inlet conduit 62. The tip of the central part 64 is located relatively close to the membrane 65. The check valve consequently is open in the normal state, allowing communication between the interior of the pump chamber and the needle 5.

If there is a liquid in the pump chamber, the membrane 65 will immediately be pressed against the tip of the conical, central part 64 by the immediate hydrostatic pressure acting on the membrane 65 which will be the consequence of a pump stroke, this because of the incompressibility and relatively high viscosity of liquids (as compared with air), thus sealing the inlet conduit 62 against a flow from the pump chamber through the inlet 62 as soon as the pressure increases at the beginning of a pump stroke. The build-up of pressure in the recess behind the membrane 65 will be slow compared to the build-up of the pressure within the pump chamber, this being a result of the viscosity of the liquid and the small size of the opening 66 (which does not need to be larger than the cross-sectional area of the inside of the needle 5).

If there is air in the pump chamber, the pressure will not build up fast enough to prevent the air to pass through the opening 66 and the inlet conduit 62, this in view of the compressibility of the air. The membrane will thus be prevented from sealing against the central part 64, allowing the air to pass the check valve.

An indicator means 26, see FIG. 1, indicating whether the pump chamber contains liquid or gas during the pumping action is arranged in a channel 25 in the side wall of the pump chamber. The means is in the form of a domed membrane 26 which is convex when viewed from the interior of the pump chamber and is held by means of a circumferential bead 27 locked in a groove 34 by means of an edge 35 crimped over the groove 34 and the bead 27. If the pump chamber contains liquid during the pumping action, the domed membrane 26 will buckle outwardly during each stroke of the pump due to the increase of the hydrostatic pressure in the incompressible liquid, whereas the domed membrane will not be affected when there predominantly is air in the pump chamber, due to the compressibility of the air.

A device sensing the movements of the domed indicator membrane 26 may be provided which device may give a warning or shut off the pump if the domed membrane does not move after a predetermined number of pump strokes.

An axially oriented outlet 23 is arranged in the side wall 21 of the pump chamber for connection to an infusion tubing. The outlet 23 is provided with check valves 24, 24' allowing liquid to flow outwardly from the pump chamber but not into the chamber.

The check valves 24, 24' are more clearly illustrated in FIGS. 2 and 3. The check valves 24 and 24' each comprise a stem part 36 respectively 36' which is held in a complementary hole 37, 37' in a respective perforated partition wall 38, 38'. Each stem part 36, 36' is joined to a respective tip of a conically flaring, resilient membrane 39, 39' located downstream in relation to the stem, downstream being defined by means of the direction of flow in use. The free edges of the conical membranes 39, 39' resiliently engage the walls of the outlet. By these means a hydraulic pressure downstream the respective valve on the inside of the conically flaring membrane will press the edges of the membrane outwards against the walls thus preventing a backward flow into the pump chamber through the outlet.

The outlet may also be provided with a restriction giving a resistance to a liquid flow which is greater than the resistance in the smallest standard injection needle used in infusion systems. The reason for this restriction is that in some cases it may be desirable to provide a predetermined, constant resistance against which the pump works. The resistance may of course be designed as a set of separate parts mountable in the outlet in dependence of the greatest resistance expected in the infusion tubing. One embodiment of the restriction may for instance be an air filter. The check valves 24, 24' may also serve as the restrictions discussed above, for instance by choosing the stiffness of the membranes 39, 39' or the cross-sectional area of the perforations in the partition wall in accordance with the required restriction.

As for instance can be seen in FIG. 3, an indicator means 50 for indicating a blockage in the infusion tubing, for instance due to a bend the infusion tubing, is located in a conduit 55 connected to the outlet 23 between the two check valves 24, 24'. The means 50 is similar to the indicator means 26 and consequently is in the form of a domed membrane 51 which is convex seen from the interior of the outlet and is held by means of a circumferential bead 52 locked in a groove 53 by means of an edge 54 crimped over the groove 53 and the bead 52.

Should there be a blockage in the infusion tubing, the pressure in the space between the two check valves 24, 24' will rise and the domed membrane 51 will buckle outwardly, thus indicating an abnormal condition. The domed membrane may also be connected to a sensor means sensing the movement of the domed membrane in order to give a warning signal or to switch off the pump upon a movement of predetermined size.

Figure 6:
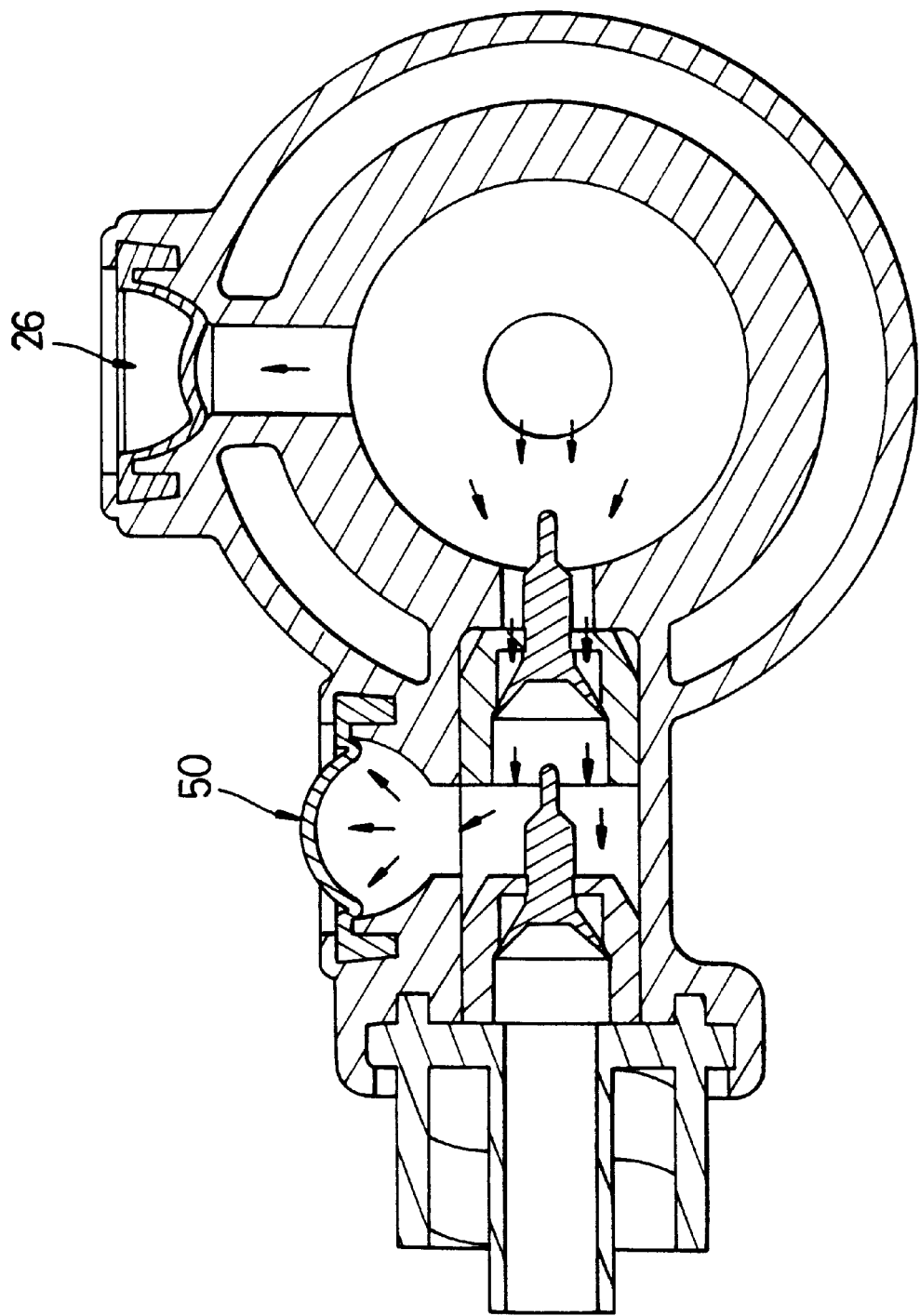
FIG. 6 illustrates the function of the indicating membranes.

The function of the two indicator means 26 and 50 are more clearly illustrated by means of the arrows in FIG. 6.

Figure 5A:
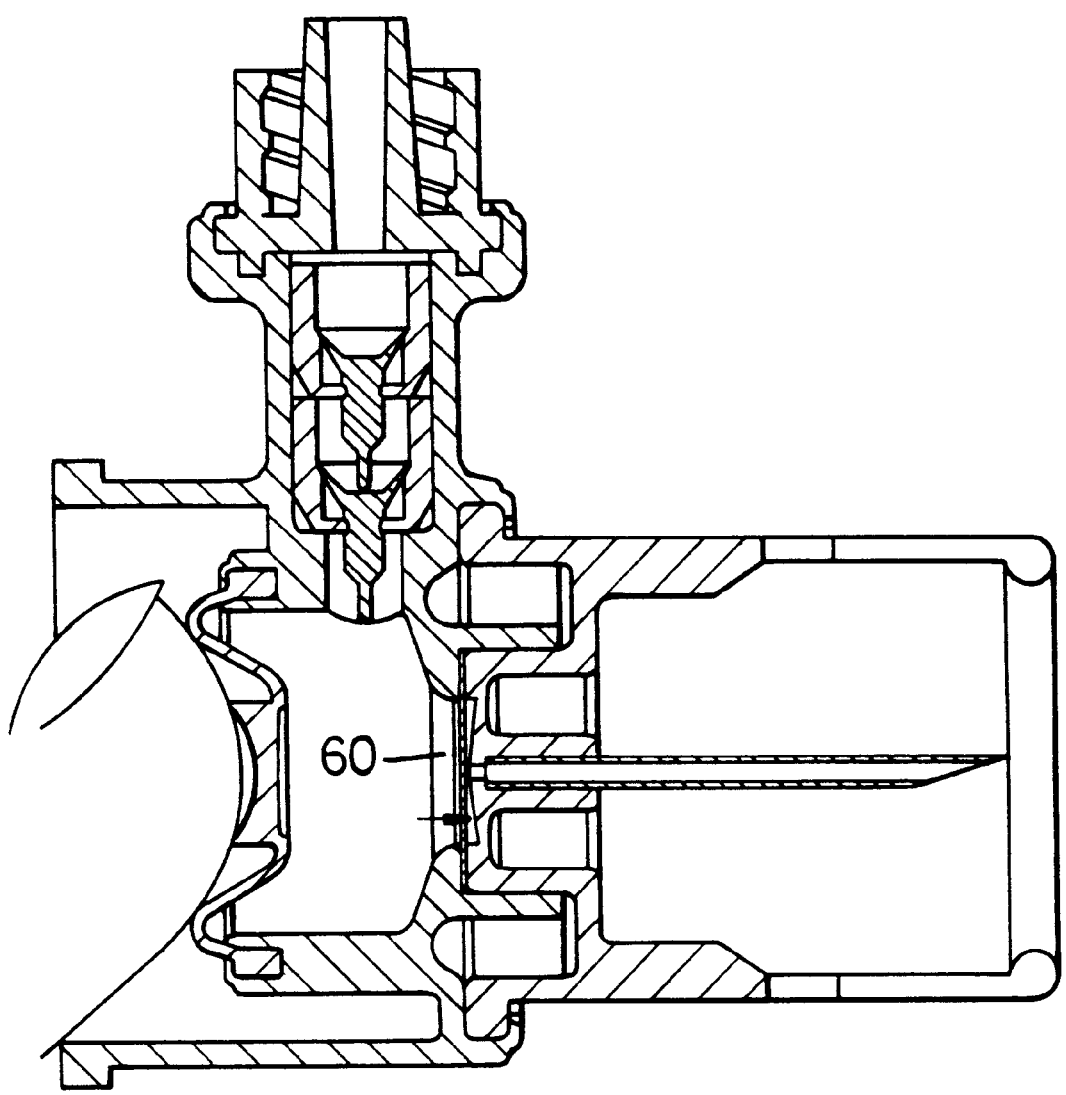
FIGS. 5A–5E illustrate the function of the pump chamber.

When the pump chamber is to be used in an infusion system, a pump chamber is taken from a sterile package and an infusion bag containing the active composition to be administered is connected to the inlet and the infusion tubing is connected to the outlet of the pump chamber. The tubing is not yet connected to the patient. FIG. 5A illustrates how the domed pump membrane can be used manually to empty the pump chamber from air and fill the chamber with liquid and subsequently to fill the entire infusion tubing with liquid. By means of the large-stroke, manual compression of the domed membrane, a large part of the sterile air in the pump chamber will be forced through the check valve 60 and the inlet conduit into the infusion bag. When the membrane is released, the domed membrane will snap back to its original shape, sucking liquid from the infusion bag through the inlet. In this way, the air in the pump chamber will be removed in a fast and reliable way and replaced by liquid from the infusion bag.

As soon as the air in the pump chamber has been removed and has been replaced fully by liquid, the check valve 60 will close immediately when the pressure in the chamber starts to increase as a result of a pump stroke. The liquid present in the pump chamber will then be pumped out through the outlet at each manual or mechanical pump stroke. The large stroke manual actuation of the domed membrane is then continued until the liquid flows continuously out of the injection needle (or any other connecting means to the patient used). This indicates that the entire infusion system contains liquid and is free from air and can be connected to the patient.

Figure 5B:
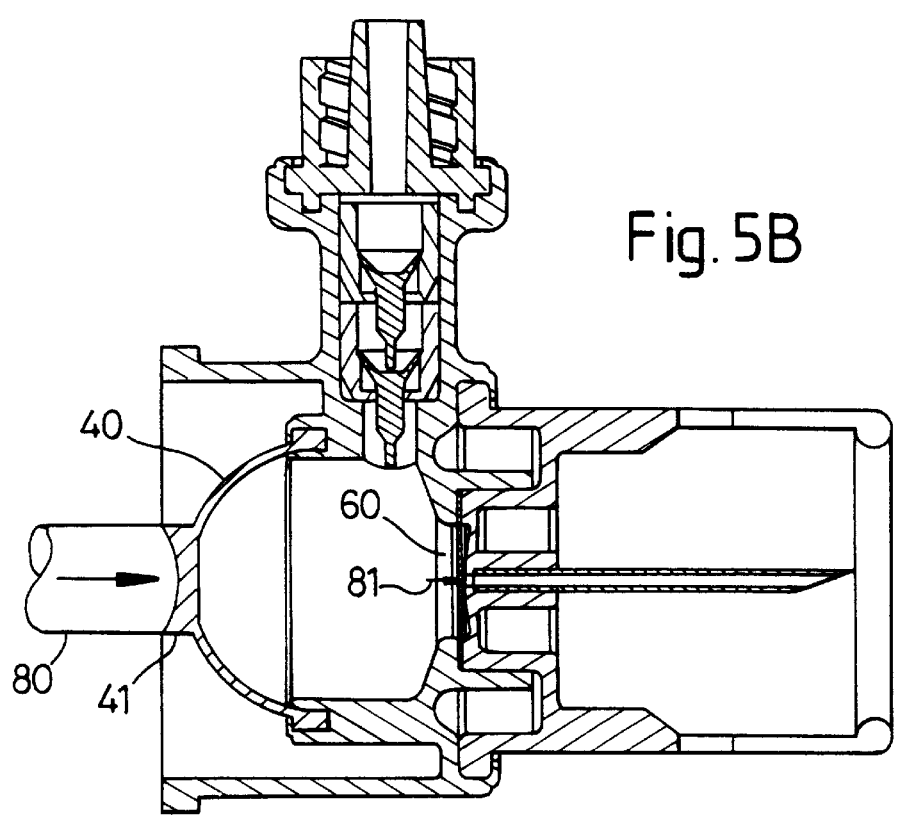
Figure 5C:
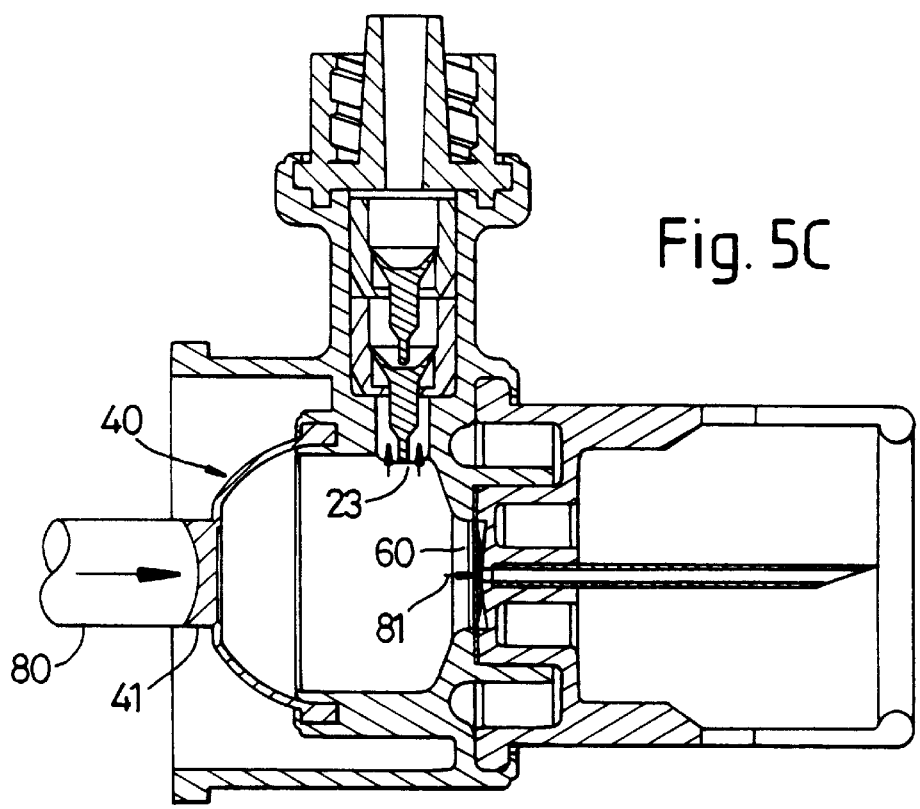
Figure 5D:
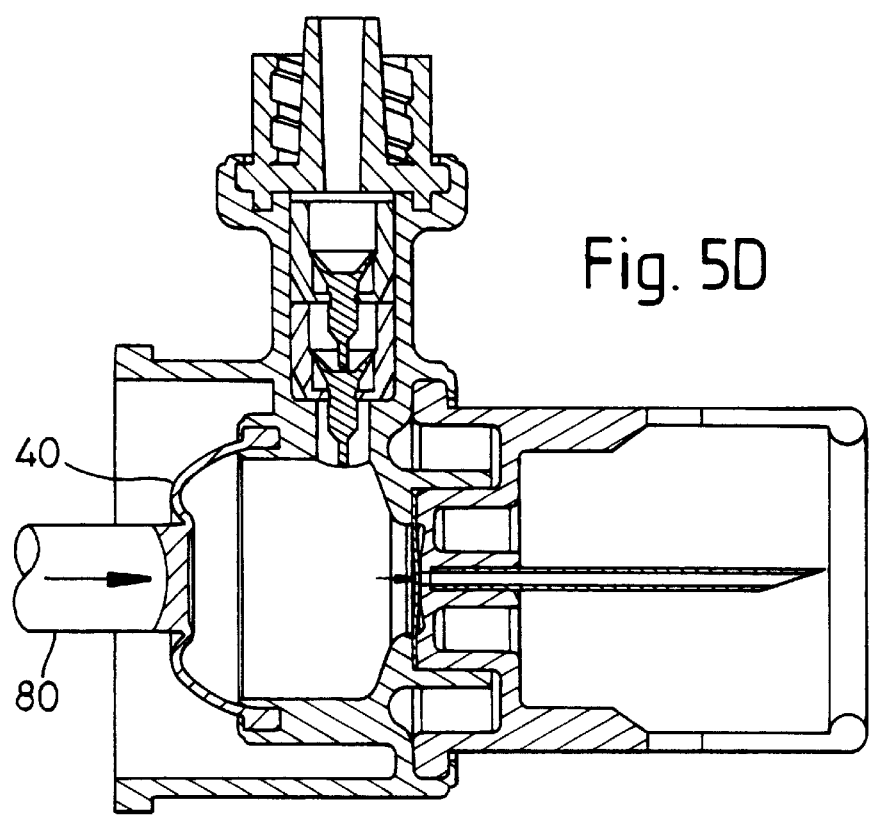
Figure 5E:
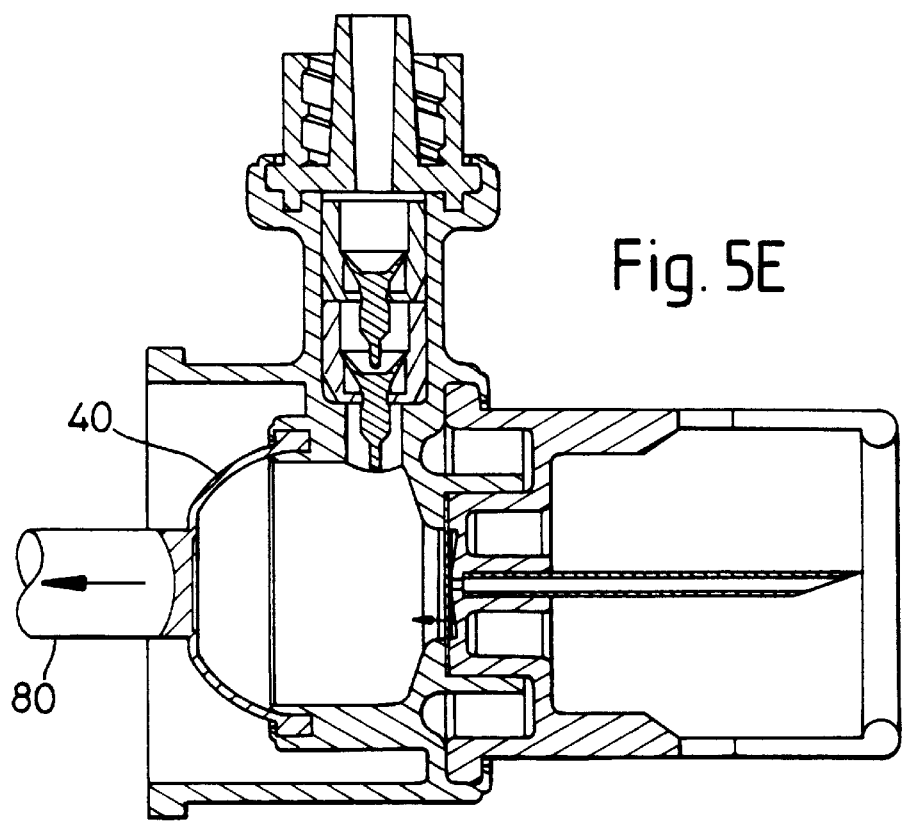

The pump chamber is then inserted into a pump driving means which has means positioning the pump chamber and the domed membrane 40 exactly relative to a reciprocally movable piston 80 (See FIG. 5B). When the infusion pump is to be used, the driving means is switched on and the piston moves a predetermined distance against the plate 41 on the apex of the domed membrane 40. This distance is set in dependance of the amount of liquid to be administered at each stroke of the pump. The intervals between each stroke is predetermined and set in dependence of the amount of liquid to be administered over a certain length of time.

As soon as the piston starts to move, the pressure in the pump chamber increases and the check valve closes as described above, see the arrow 81 in FIGS. 5B and 5C. The domed membrane is deformed (buckled) as a result of the movement of the piston and an amount of liquid corresponding to the net decrease of the volume of the deformed dome is pumped through the outlet 23 and into the infusion tubing to the patient, see FIGS. 5C and 5D. The pressure in the pump chamber will thus be equalized. When the piston 80 starts to move backwards, the pressure in the pump chamber will be lower than ambient pressure due to the resilience of the domed membrane which resumes its original shape, see FIG. 5E. This means that the pressure in the infusion tubing will be higher than the pressure in the pump chamber and the check valves in the outlet close. Consequently liquid will be drawn into the pump chamber from the infusion bag through the inlet 22, past the check valve 60 until the domed membrane entirely has resumed its original shape.

The combination of the elasticity and the domed shape of the membrane will ensure that the membrane distinctly and rapidly snaps back from its buckled condition to its original shape, following the actuating piston during the backward movement thereof whilst exerting a relatively constant suction upon the liquid in the pump chamber during the entire movement. This means that the volume of the liquid drawn into by the membrane in connection with each individual pump stroke will be both exactly defined and drawn into the pump chamber fast enough to ensure that the entire volume has been drawn into the pump chamber before the next stroke of the pump.

Should the infusion bag become empty, the pump will suck some air into the pump chamber. The presence of air in the pump chamber will however entail that the pump immediately stops working, since each subsequent pump stroke merely will move air to and fro through the check valve 60 in the inlet, which is open to air as discussed above. This will prevent air from being pumped into the infusion tubing and, ultimately, to the patient. An indication that the infusion bag is empty is also given by the indicator means 26, as discussed above.

Should the infusion tubing be blocked by a bend in the tubing or by an object, the indicator means 50 will indicate this, as also discussed above.

One example of a combination of materials and dimensions which would give the domed membrane the desired resilience and rigidity could be as follows:

Material: Polyethylene
Inner radius: 7.4 mm
Thickness: 0.5 mm

These dimensions and materials would naturally be varied in dependence of the desired capacity range of the pump. The preferred material in the membranes generally is polyethylene although polypropylene also is suitable in some applications. In the remaining parts of the pump chamber the preferred material is polypropylene.

Figure 7:
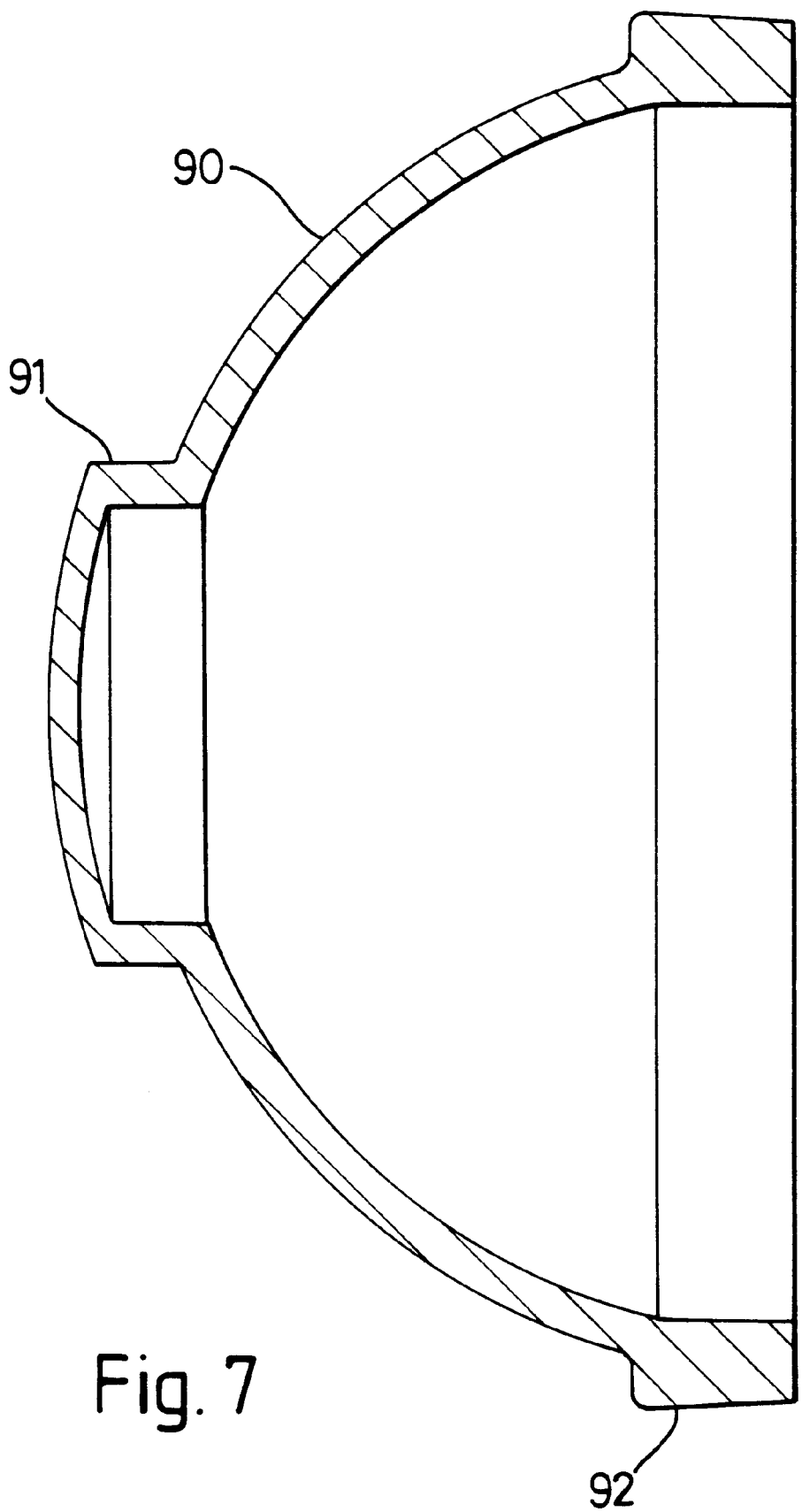
FIG. 7 shows an alternative embodiment of a pump membrane in section.

An alternative design of the pump membrane is shown in FIG. 7. In this embodiment the apex of the domed membrane (90) is provided with a secondary, smaller dome (91) projecting outwardly from the domed membrane (90) and formed integrally with the domed membrane. The size of the secondary dome (91) may adapted to the volume of the dose of the composition to be administered by each stroke of the actuating means. The domed membrane also includes a bead (92) for mounting the membrane in the groove (29) in the wall (21) of the pump chamber.

Figure 8:
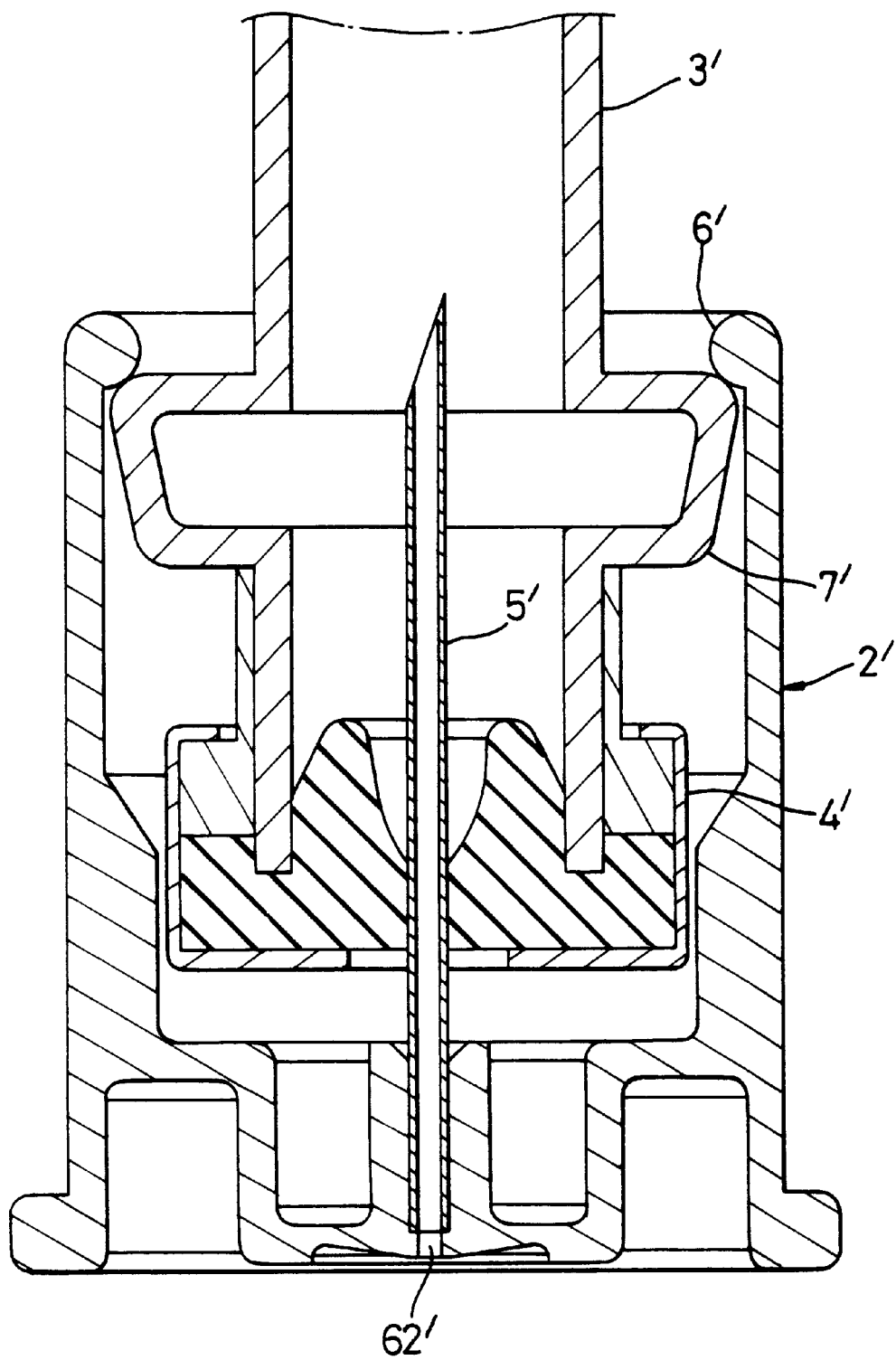
FIG. 8 illustrates an alternative embodiment of the parts of the pump chamber serving as connection means to the source of liquid.

FIG. 8 illustrates a second embodiment of a tubular connecting part 2' for connection to a standard infusion bag 3'. Again the infusion bag 3' is provided with a standard rubber or plastic seal 4' to be penetrated by a hollow, standard type needle 5' located within the connecting part 2'. The connecting part 2' also includes retaining means 6' in the form of a circumferential bead engaging a flange portion 7' on the infusion bag. In this embodiment the retaining means 6' are not designed to damage the connecting part 2'.

Where it is desirable, from the point of view of safety, that neither the pump chamber nor the infusion bag 3' are reused, the needle 5' may be slidably mounted in the inlet conduit 62', the friction between needle and conduit being chosen to be lower than the friction between needle and seal 4' when the seal is mounted upon the needle. In this way the needle will be removed together with the infusion bag, Alternatively, the seal 4' may be fabricated from material (eg rubber) to be pierced by the needle 5', which once pierced provides significant resistance to translational movement of the needle in the direction of the pump chamber. The needle 5' may further be frangibly connected to the inlet conduit 62'. In this way if it attempted to remove the pump chamber from the infusion bag 3', the needle is retained in the seal 4' and neither can be reused.

The domed membrane has been described as being spherical in shape. Other domed shapes which give the desired distinct movement or resumption of the original shape may also be used.

The pump chamber as claimed in the appended claims and as described above will be simple to manufacture and use whilst being exact and reliable. The chamber will also be inexpensive enough in manufacture to allow the chamber to be fully disposable after use.

By means of the pump chamber a infusion pump further is obtained which readily is usable with standard, prefilled infusion bags, and which can be used both stationary, for instance in hospitals and mobile, carried by the patient. The pump chamber is designed to allow the infusion bag to be connected directly to the bag, without any need for extra tubing.

The pump chamber consequently has considerable advantages in regard of safety, economy and handling, both for patients and for hospital staff.

We claim:

1. Pump chamber for a pump for the administration of active compositions, said pump chamber comprising:
   walls delimiting said pump chamber, wherein said walls define an inlet and an outlet, a part of said walls of said pump chamber being formed by a flexible membrane, said membrane being actuatable by a reciprocally movable actuating means that varies the volume of the pump chamber in accordance with the movements of said actuating means, said membrane having a convex domed shape projecting outwardly from said pump chamber and being made of a resiliently flexible material, the apex of the membrane being acted upon by said actuating means, said actuating means having a stroke which is adjustable to the amount of dose to be administered; and a tensioned, planar membrane positioned over said inlet and allowing air to pass in and out of the pump chamber, but blocking a liquid flow through the inlet from the pump chamber.

2. The pump chamber as claimed in claim 1, wherein the apex of said membrane is provided with a plate, formed integrally with said membrane and located on the outside of said membrane, that is acted upon by said actuating means.

3. The pump chamber as claimed in claim 2, wherein said membrane contains a secondary, smaller dome projecting outwardly from said membrane and formed integrally with said membrane, the size of said secondary dome being adapted to the volume of the dose of the composition to be administered by each stroke of the actuating means.

4. The pump chamber as claimed in claim 3, wherein said plate is symmetrical relative to the apex of said membrane and is provided with a concave shape corresponding to a convex shape on said actuating means.

5. The pump chamber as claimed in one of claims 1–3 and 4, wherein said inlet and said outlet are orthogonal to one another.

6. The pump chamber as claimed in one of claims 1–3 and 4, wherein said actuating means is a reciprocally and longitudinally movable piston.

7. The pump chamber as claimed in claim 6, wherein said actuating means comprises a rotatable shaft having one end in contact with one end of said piston, wherein said piston is located along the axis of rotation of said shaft and is free to move translationally along, though not to rotate about, the axis of rotation of said shaft, and a means for maintaining contact between said shaft and said piston and cam surfaces at the contacting ends of said piston and said shaft, such that rotation of the shaft, coupled with the means for maintaining contact between said shaft and said piston, enables the piston to move reciprocally.

8. The pump chamber as claimed in claim 7, wherein said means for maintaining contact between said shaft and said piston comprises said membrane.

9. The pump chamber as claimed in one of claims 1–3 and 4, wherein said check valve covers a recess surrounding said inlet, said planar membrane having an opening, said recess being provided with a projecting part extending towards but spaced from the planar membrane and containing an inlet conduit located at a distance from the walls of said recess and at a distance from said opening.

10. The pump chamber as claimed in claim 9, wherein said projecting part has an end that comes to a point, and said conduit being located in the end of the projecting part that comes to a point.

11. A check valve for an inlet of a pump chamber, comprising:

a planar, resilient membrane tensioned over a recess surrounding a conduit spaced apart from said planar membrane, said conduit located in said recess, said planar membrane having an opening located within the area of the recess that is offset in relation to said conduit.

12. A check valve as claimed in claim 11, wherein said conduit is located in a central part that has an end that comes to a point, and said conduit being located in the end of the central part that comes to a point.

* * * * *